United States Patent
Zhou et al.

(10) Patent No.: US 6,713,038 B2
(45) Date of Patent: Mar. 30, 2004

(54) TIO₂ COMPOUNDS OBTAINED FROM A HIGH SILICA CONTENT ORE

(75) Inventors: Ling Zhou, Severna Park, MD (US); Thomas Messer, Columbia, MD (US); Fu-Chu Wen, Severna Park, MD (US); Mark Banash, Hanover, MD (US)

(73) Assignee: Millenium Inorganic Chemicals, Inc., Hunt Valley, MD (US)

( * ) Notice: Subject to any disclaimer, the term of this patent is extended or adjusted under 35 U.S.C. 154(b) by 273 days.

(21) Appl. No.: 09/829,616

(22) Filed: Apr. 10, 2001

(65) Prior Publication Data

US 2002/0000138 A1 Jan. 3, 2002

Related U.S. Application Data (60) Provisional application No. 60/198,051, filed on Apr. 18, 2000.

(51) Int. Cl.⁷ ............................................. C01G 23/047
(52) U.S. Cl. ........................ 423/610; 423/85; 423/69; 241/14; 241/15; 241/20
(58) Field of Search .................... 423/69, 85, 610, 423/80–86; 241/14, 15, 20; 209/5

(56) References Cited

U.S. PATENT DOCUMENTS

| | | | |
|---|---|---|---|
| 2,312,466 A | 3/1943 | Erickson et al. | |
| 2,362,432 A | 11/1944 | Cahn | |
| 2,494,139 A | 1/1950 | Moyer | |
| 3,701,421 A | 10/1972 | Maxwell | |
| 3,857,781 A | 12/1974 | Maynard | |
| 4,052,223 A | 10/1977 | Howard | |
| 4,193,767 A | 3/1980 | Fipke | |
| 4,268,380 A | 5/1981 | Shaw | |
| 4,339,331 A | 7/1982 | Lim et al. | |
| 4,725,358 A | 2/1988 | Ananthapadmanabhan et al. | |
| 5,154,767 A | 10/1992 | Kunkle et al. | |
| 5,234,883 A | 8/1993 | Schaefer-Sindlinger et al. | |
| 5,389,355 A | * 2/1995 | Gueguin | 423/610 |
| 5,411,149 A | 5/1995 | Chaiko et al. | |
| 5,584,394 A | 12/1996 | Behl et al. | |
| 5,603,411 A | 2/1997 | Williams et al. | |
| 6,375,923 B1 | * 4/2002 | Duyvesteyn et al. | 423/610 |

FOREIGN PATENT DOCUMENTS

| | | |
|---|---|---|
| EP | 0529190 A1 | 3/1993 |
| WO | WO 95/28502 | 10/1995 |

OTHER PUBLICATIONS

XP–002181574, Derwent Publications Ltd., London, GB; AN 1995–077871, (1995).
XP–002181575, Derwent Publications Ltd., London, GB; AN 1995–221477 (1995).

(List continued on next page.)

Primary Examiner—Stuart L. Hendrickson
Assistant Examiner—Anthony J Kuhar
(74) Attorney, Agent, or Firm—Kalow & Springut LLP; Scott D. Locke, Esq.

(57) ABSTRACT

A titanium dioxide compound was isolated from a rare type of naturally occurring ore. Processes for efficiently isolating and obtaining these TiO₂ compounds, as well as methods for using them have been developed. These TiO₂ compounds may be used directly in applications such as paper, plastics and paints without being subjected to the chloride or sulfate processes. Also they made be used as a feedstock for the chloride or sulfate processes. In order to obtain these TiO₂ compounds, one may grind or pulverize the naturally occurring ore, disperse it in a solution or suspension, and process it by selective flocculation or aqueous biphasic extraction.

18 Claims, 2 Drawing Sheets

OTHER PUBLICATIONS

Chaiko, et al., "Metal Separations Using Aqueous Biphasic Partitioning Systems," Emerging Separation Technologies for Metals II, Ed. by R.G. Bautista, The Minerals, Metals & Materials Society, pp. 171–185 (1996).

Osseo–Asare, et al., "Aqueous Biphasic Extraction of Particulates: Controlling the Hydrophilic–Hydrophobic Balance for Separations," Metal Separation Technologies Beyond 2000: Integrating Novel Chemistry With Processing, Eds. K.C. Liddell and K.J. Chaiko, The Minerals, Metals & Materials Society, pp. 347–355 (1999).

The Encyclopedia of Chemical Technology, Kirk–Othmer, 4th ed., vol. 24, pp. 247–248.

The Encyclopedia of Chemical Technology, Kirk–Othmer, 4th ed., vol. 18, pp. 10–11.

Lange's Handbook of Chemistry, 14th ed., pp. 8.106–8.110.

* cited by examiner

TIO₂ COMPOUNDS OBTAINED FROM A HIGH SILICA CONTENT ORE

CROSS-REFERENCE TO RELATED APPLICATION

This application claims the benefit of the filing date of U.S. Provisional Application No. 60/198,051, which was filed on Apr. 18, 2000 and is entitled: "Methods for Separating and Using High Purity Titanium Dioxide Obtained from a High Silica Content Ore." The entire disclosure of that application is hereby incorporated by reference into the present disclosure.

BACKGROUND OF THE INVENTION

The present invention relates to the field of ore processing. More particularly, the invention relates to the beneficiation of naturally occurring ores consisting essentially of titania and silica compounds and uses of these processed ores. By the methods of the present invention, from these ores, one may isolate high purity unique $TiO_2$ compounds. These compounds may be used directly in many of the products and processes that traditional sources of $TiO_2$ are used without being subjected to more traditional and burdensome processes such as the chloride and sulfate processes. Because the $TiO_2$ compounds of the present invention are produced more economically than $TiO_2$ is typically produced, these $TiO_2$ compounds offer attractive options for manufacturing $TiO_2$ containing products.

Naturally occurring ore that contains titania compounds, such as $TiO_2$, typically is not suitable for direct extraction of pigmentary and subpigmentary sized $TiO_2$ particles. The physical and chemical compositions of most ores that contain titania, for example, ilmenite, require that ore be processed via either the "chloride" or the "sulfate" methods in order to convert the titanium compounds found in the ore into intermediate chemical forms, such as titanium tetrachloride or titanyl sulfate, prior to conversion into particles of $TiO_2$ useful for industrial applications. Thus, most ores do not lend themselves to direct extraction and incorporation into products.

Processing ore via the "chloride" and "sulfate" methods is both costly and labor intensive, requiring significant capital investment in equipment and personnel. Consequently, there is a need to develop less expensive methods for obtaining commercially useable $TiO_2$ and $TiO_2$ concentrates.

Certain ore deposits, for example, ore deposits in Peru near the town of Tacna on the Peruvian-Chilean border approximately 86 km to the northeast of Tacna, contain titania particles of varying sizes and crystal aggregations in a matrix of essentially crystalline silica. These titania particles contain both rutile crystals and anatase crystals, and typically are approximately 40% rutile crystals and 60% anatase crystals, but they may contain between 15–50% rutile and 50–85% anatase crystals.

Traditional ore processing and separation techniques are not efficient in separating the titania and silica components of this type of ore. This type of naturally occurring ore, regardless of where it is found in the world, is referred to herein as "Tacna-type ore." The amount of titania and silica, as well as the other parameters of Tacna-type ore are more fully described in the detailed description below.

In order to separate the titania particles from the silica matrix of Tacna-type ore, a series of processing steps were needed. Once Tacna-type ore is processed, a compound that contains a greater percentage of the $TiO_2$ compound may be isolated. The phrase "$TiO_2$ compound" as used herein refers to any ore that has been processed from Tacna-type ore so as to increase the relative percentage of titania to other particles to above about 50% by weight.

The $TiO_2$ compounds of the present invention thus offer novel and efficient methods of processing $TiO_2$ for use in many applications in which $TiO_2$ is currently used, including in paper, plastics and coating applications, as well as in other applications such as catalysts and sunscreens. Because the processes that were developed are more cost effective than traditional processing techniques, less expensive products containing $TiO_2$ may be produced.

SUMMARY OF THE INVENTION

The present invention relates to processes for obtaining $TiO_2$ compounds from Tacna-type ore, the methods for using these $TiO_2$ compounds, and these $TiO_2$ compounds themselves.

Under one embodiment, the present invention provides a process for obtaining the $TiO_2$ compounds from Tacna-type ore that may be used directly in many applications without the use of the burdensome chloride or sulfate process. This method comprises:

a. grinding a Tacna-type ore to form ground ore having particles of a size suitable to form an aqueous slurry;

b. combining the ground ore, water and a separating agent so as to form an aqueous slurry of constituents; and c. separating the constituents of the aqueous slurry to isolate the $TiO_2$ compounds.

The separating step may be accomplished by a number of methods, including selective flocculation and biphasic extraction, such as with polyglycolic compounds. These methods may be used alone or in combination.

The $TiO_2$ compounds that have been processed by this method may be used in a variety of applications. For example, the $TiO_2$ compounds may be further processed in a manner so as to isolate the ultrafine sized titanium dioxide particles for direct use in applications such as sunscreens and automobile catalysts. Further, the $TiO_2$ compounds may be used directly in many paper, plastics and coatings applications. Moreover, the $TiO_2$ compounds may be used alone, or blended with other ores that are not Tacna-type ores and used as feedstock in either the sulfate or the chloride processes for the production of $TiO_2$ pigments that can be used in papers, plastics and coatings applications.

Under another embodiment, the present invention relates to the isolated and purified $TiO_2$ compound itself, which is formed by the beneficiation of Tacna-type ore. These $TiO_2$ compounds consist essentially of silica and titania wherein the titania is at least about 50% by weight of the $TiO_2$ compound. The titania consists essentially of rutile and anatase crystals, wherein the weight of the rutile crystals is preferably between about 30% and about 50% of the total titania.

BRIEF DESCRIPTION OF THE FIGURES

FIG. 2B is a representation of a higher magnification of a section of FIG. 2A.

DETAILED DESCRIPTION OF THE INVENTION

The present invention provides an economical method for isolating a commercially useable $TiO_2$ compound from a rare type of naturally occurring ore, methods for using this $TiO_2$ compound and the compound itself. The $TiO_2$ compounds obtained via the present invention may be used in a variety of different applications. For example, ultrafine particles can be obtained from the $TiO_2$ compounds and may be used directly in applications such as sunscreens and automobile catalysts. The $TiO_2$ compounds may also be used directly in industrial applications, including as additives in paper, plastics and coatings, as well as in other applications that are now known or come to be known by persons skilled in the art. Further, the $TiO_2$ compounds may be used as a feedstock in either the sulfate or the chloride processes.

The present disclosure is not intended to be a treatise on either ore processing or pigments. Readers are referred to appropriate available texts and other materials in the field for additional and detailed information on any aspect of practicing this invention.

Tacna-type Ore

Tacna-type ore contains essentially of only silica and titania. Preferably, at least 95% of the Tacna-type ore will be silica and titania, more preferably, at least 98% of the ore will be silica and titania, and most preferably, at least 99% of the ore will be silica and titania. The titania particles of the ore typically have intrinsic sizes of from about 0.01 microns to about 4 microns while the silica particles typically have sizes from about 0.4 microns to about 60 microns. The titania component of the ore is typically more than 98 percent pure. The titania concentration of Tacna-type ore has been found to vary from typically about 4 percent to about 30 percent by weight, based on the weight of the naturally occurring ore. Surprisingly, there are significant amounts of both rutile and anatase crystals within the titania. There can be between about 15 and about 50% rutile crystals and between about 50 and about 85% anatase crystals. Typically, the titania contains approximately 30–50% rutile crystals and approximately 50–70% anatase crystals.

Tacna-type ore may also contain small amounts of other substances such as substances that contain iron, but at least a significant portion of the ore consists of silica and titania. If the Tacna-type ore contains iron containing substances, these substances will preferably be in the form of $Fe_2O_3$ and will be in an amount less than 0.5% by weight of the Tacna-type ore.

Figure 2A:
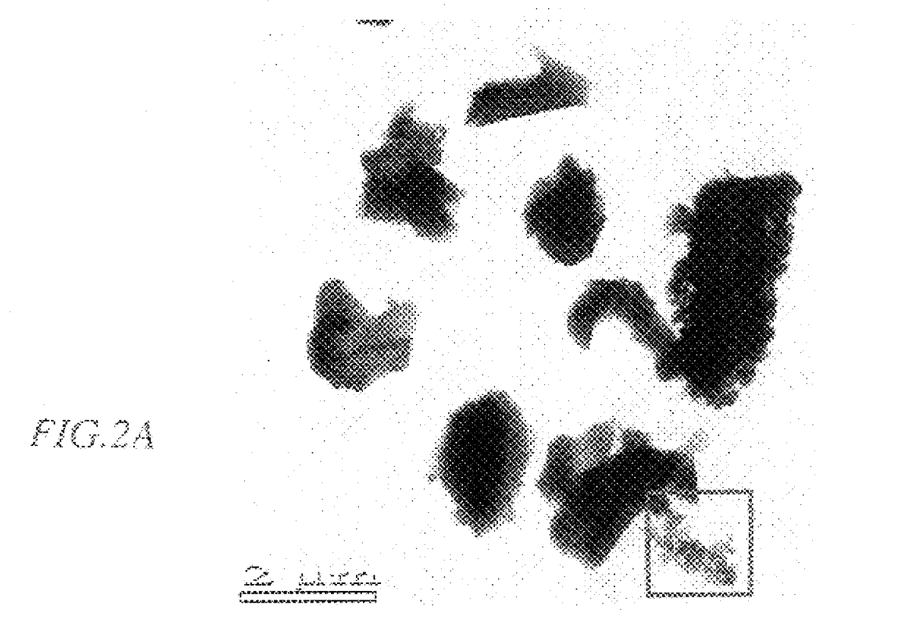
FIGS. 2A and 2B are representations of TEM high magnification images of the Peruvian deposit, showing naturally occurring ore samples from Tacna, Peru that have Tacna-type ore.
Figure 2B:
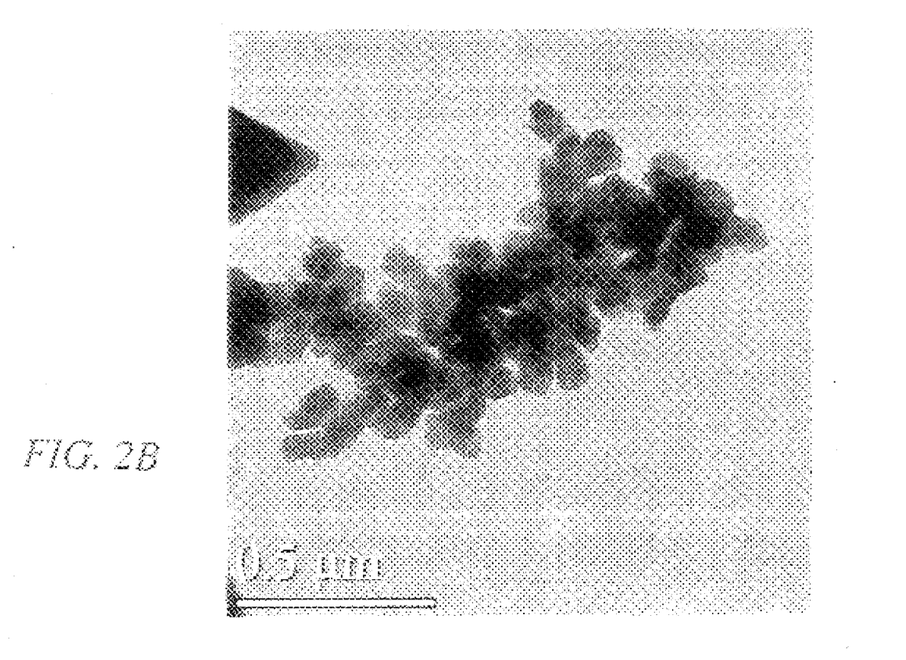

FIGS. 2A and 2B, which are representations of TEM high magnification images of the Peruvian deposit, show naturally occurring ore samples from Tacna, Peru. The figures demonstrate how the ore may appear in its natural state; particles of titania exhibiting various sizes exist in what is essentially a silica matrix. FIG. 2B is a higher magnification of a section of FIG. 2A.

The $TiO_2$ Compounds

The $TiO_2$ compounds of the present invention are obtained by processing Tacna-type ore. Because of the Tacna-type ore's structure and components, it was necessary to develop processes in order to obtain the $TiO_2$ compounds. The $TiO_2$ compounds that are obtained by the present invention are obtained more economically than processed $TiO_2$ that is obtained from other sources, such as through either the chloride or the sulfate processes, because one does not need to convert chemically the $TiO_2$ into an intermediate substance and then back into $TiO_2$ as one does in these other processes. Surprisingly, the $TiO_2$ compounds may be used in many of the same processes and products as $TiO_2$ that is processed by these more traditional methods.

Figure 1:
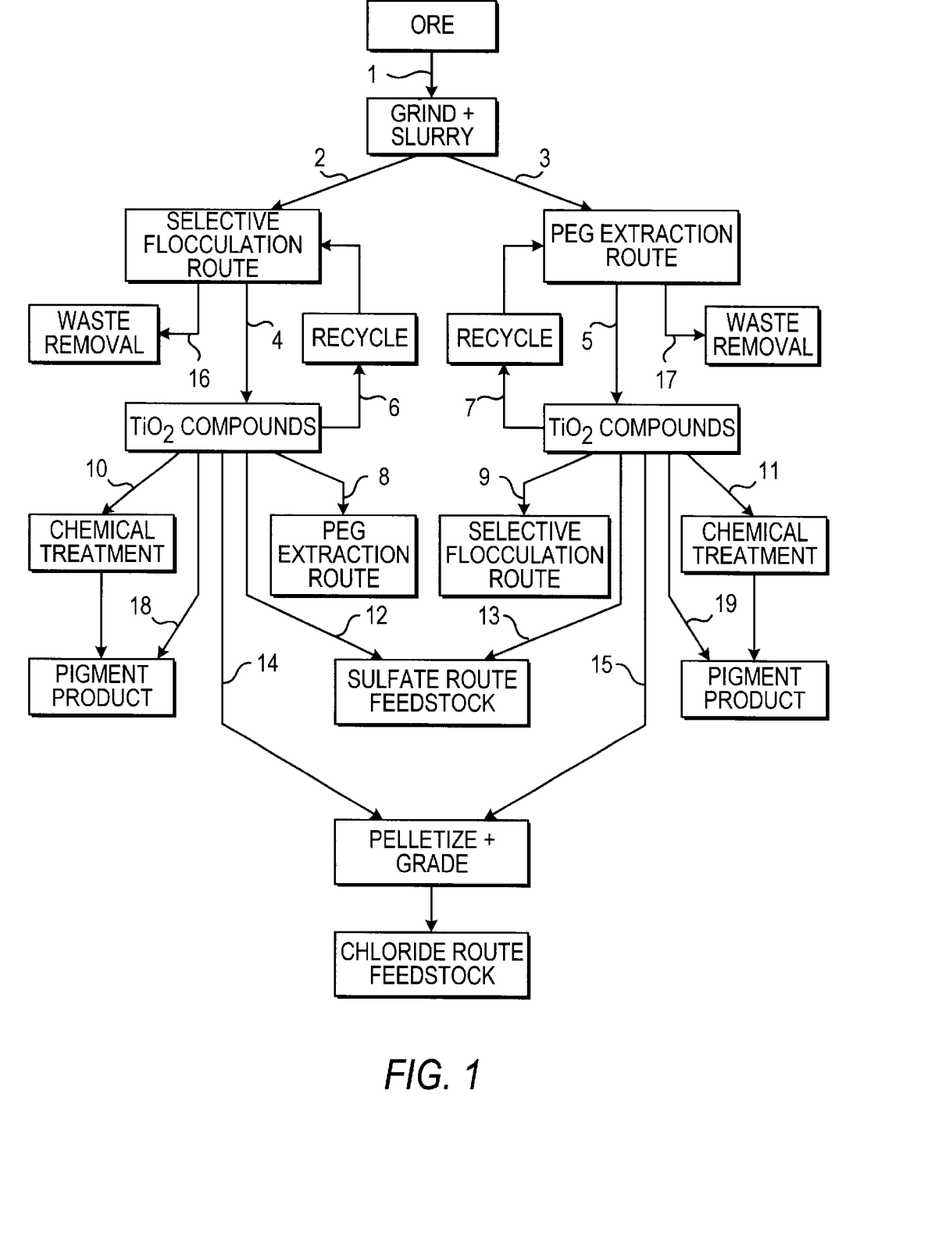
FIG. 1 is a block diagram that illustrates an ore processing scheme of the present invention that may be used to produce $TiO_2$ compounds from Tacna-type ore. The figure also illustrates several possible combinations of ore enrichment schemes using the disclosed invention.

Examples of different processing steps are shown in FIG. 1. The desired concentration of $TiO_2$ in the $TiO_2$ compounds from the present invention will depend on how the titanium dioxide will be used or in what application it will be used. The processing steps may be repeated and/or combined in sequence in order to obtain higher concentrations of $TiO_2$ in the $TiO_2$ compounds. The phrase "$TiO_2$ compound" refers to a compound that contains at least about 50% $TiO_2$, but preferably at least about 80% $TiO_2$, more preferably, at least about 90% $TiO_2$.

In accordance with the present invention, Tacna-type ore is initially processed into a form that will allow it to be slurried or placed in a suspension. For example, the ore may be pulverized, ground or otherwise made into smaller and more easily dispersed particles. The terms "grinding" and "ground" as used herein include pulverizing, making or otherwise producing smaller and more easily dispersed particles that are of a size suitable to be used in an aqueous slurry. Methods for generating these smaller and more easily dispersed particles include sand milling and other such media milling, including micronizing or fluid energy milling, ball milling and hammer milling. Other methods suitable for generating the particles are known or easily determinable by persons skilled in the art. Preferably, the ground ore contains Tacna-type $TiO_2$ particles that have intrinsic sizes of from about 0.01 microns to about 4 microns.

After the naturally occurring ore has been ground into suitable $TiO_2$ particles, an aqueous slurry is formed by combining the ground particles, water and a separating agent. The components of the aqueous slurry may be referred to as "constituents." The phrase "aqueous slurry" as used herein refers to any suspension, solution or other combination of substances comprising water, ground particles and a separating agent. The phrase "separating agent" includes any substance that may be used to separate the solid $TiO_2$ particles from the other components or constituents of the aqueous slurry and includes surfactants, dispersants, electrolytes, polyethylene glycols and other substances that are now known or that come to be known in the art and that are effective at separating the solid $TiO_2$ particles from the other components or constituents of the aqueous slurry. Preferably, the aqueous slurry contains from about 20% to about 60% solids based on the weight of the slurry.

Once the aqueous slurry has been formed, one must separate the solid $TiO_2$ particles, from the remainder of the aqueous slurry. This requires the coagulation and isolation of a precipitate. According to the present invention, this may be done by employing, alone or in combination: selective flocculation, biphasic extraction such as polyglycol extraction, or equivalent techniques.

In some embodiments of the invention, selective flocculation using surfactants and dispersants and optionally, electrolytes or buffering systems, may be used to isolate the $TiO_2$ particles effectively from the other components or constituents of the aqueous slurry. Flocculation as a technique involves precipitating coagulates and is well known to persons skilled in the art. A flocculant is a chemical or a substance that causes particles to clump together in a suspension of particles. Flocculants that may be useful in the practice of the present invention include aluminum sulfate, polyaluminum chloride, sodium aluminate, sodium silicate, sodium sulfate, sodium metasilicate, starch, guar gum, acrylamide-acrylic polymers, polyamines, polyethylene oxide, alkyl polymers and the like.

The dispersants, surfactants, and electrolytes or buffering systems that may be used in the invention are also known or easily determinable by those skilled in the art. A dispersant is a chemical or substance that prevents particles from clumping together and forming a suspension of particles. Dispersants that may be useful include poly(meth) acrylates, polymaleates, condensed phosphates, polysulfonates, sulfonated polycondensates, tannins, lignins, glucosides, alginates and the like. In order to facilitate dispersion of the $TiO_2$ particles, one may also use suitable surfactants, including acids or bases. A surfactant is a soluble compound that reduces the surface tension of two liquids or the interfacial tension between two liquids or between a liquid and a solid. Electrolytes may also be used in the present invention. An electrolyte is an electrically conductive solution that can modify the dispersant or flocculant properties of the particle suspension. Examples of electrolytes include ions derived from the following salts: $CaCl_2$, NaCl, $Na_2SO_4$, $Na_2CO_3$, KCl, $NaNO_3$, and $NH_4Cl$. A buffering solution, which is also useful according to the present invention, is a solution that reduces pH changes when acids or bases are added to the solution. For example, hydrogen phosphate/citric acid and sodium acetate/acetic acid buffers may be used.

An aqueous biphasic extraction technique may also be employed in the invention, which is an environmentally favored means of separation. This technique may be used either alone or in combination with selective flocculation in order to separate $TiO_2$ particles from the slurry and has been found to provide high concentrations of titania. It permits the separation of titania and silica by their surface properties and is well known to those skilled in the art.

Biphasic extraction is a separation method that relies on the use of two liquids that are immiscible, and uses these liquids to segregate or to separate solid particles into the different liquid phases. Depending on the composition and properties of the solids particles, they will form suspensions in one or the other of the liquids, and the liquid phases can then be separated by for example decanting or other methods that are now known or come to be known to persons skilled in the art. According to the present invention, for biphasic extraction processes one may use a polyglycol or combinations of polyglycols, or other substances that permit effective extraction that are now known or that come to be known to persons skilled in the art. Suitable polyglycols include, for example, polyethylene glycol or PEG.

After the separation of the particles by the separating agents, coagulates or fractionates may be formed. In order to isolate the coagulate or fractionate that contains the $TiO_2$ compounds, one may use methods such as decanting and separation funnels. Other methods for isolating $TiO_2$ compounds, in general, are known or easily determinable by persons skilled in the art.

The $TiO_2$ compounds that are obtained via the present invention may be concentrated by repeatedly using the methods discussed above. Different combinations of the above steps, depending on the desired end product, may also be utilized.

FIG. 1, which is a flow chart, depicts examples of different processing steps that may be used with Tacna-type ore. As the figure depicts, the ore may initially be ground and slurried (1). It then may enter either the selective flocculation route (2) or the polyethylene glycol (PEG) extraction route (3). During these processes, waste is removed (16 & 17). After the $TiO_2$ is processed by either route, one will obtain $TiO_2$ compounds (4 & 5). The $TiO_2$ compounds can enter numerous different pathways. They can be recycled back into the same processing route (6 & 7). They can also enter a route not previously entered, i.e., the $TiO_2$ compounds obtained via selective flocculation can be processed via PEG extraction (8), and $TiO_2$ compounds obtained via the PEG extraction route can be processed via the flocculation route (9). The $TiO_2$ compounds can also be directly used as pigment products (18 & 19) or chemically treated to form pigment products (10 & 11). They can also be used as feedstock for the sulfate route (12 & 13) or the chloride route (14 & 15).

The processing of the Tacna-type ore according to the present invention, also isolates silica. This silica may be recovered and used in various applications in which silica processed by more traditional means is used.

Uses of the $TiO_2$ Compounds

Once the $TiO_2$ compounds are obtained they may be used in a number of applications including: (a) ultrafine applications; (b) paper, plastics and coatings applications; (c) feedstock applications; and (d) other applications.

a. Ultrafine Applications

After obtaining the $TiO_2$ compounds, as outlined above, one may cause the $TiO_2$ compounds to undergo classification using for example, multi-stage hydrocyclones, or other centrifuging steps known in the art to separate out particular particle size distributions to yield $TiO_2$ compounds that have specific properties, e.g., ultrafine particles useful for catalysis, etc. The desired ranges will depend on the specific desired application and are known or can readily be determined by those skilled in the art.

To produce "ultrafine" titania products, typically having a size of less than 0.1 microns, fractions of the $TiO_2$ compounds may be further processed via drying and grinding, followed by subsequent chemical treatments to make ultrafine $TiO_2$ particles that are suitable for use as products in catalysts, sunscreens and other such products or applications. In order to achieve optimum particle size distributions for the specific end uses, a variety of energy intensive grinding operations would prove suitable. These operations are readily known or easily determinable to those skilled in the art.

b. Paper Plastics and Coatings Applications

The $TiO_2$ compounds may be used as pigment products and sent directly into paper, plastics and coatings applications without further treatments. The use of $TiO_2$ as a filler with surface treatments is well known in the art and described in the *Encyclopedia of Chemical Technology*, Kirk-Othmer, 4th ed., volume 24, pp. 247 and 248, which is hereby incorporated by reference. The patent reference cited therein, U.S. Pat. No. 4,052,223, entitled, *Treatment of Pigment*, is also hereby incorporated by reference. Further, the filling and loading of papers is disclosed in *The Encyclopedia of Chemical Technology*, Kirk-Othmer, 4th ed., volume 18, pp. 10 and 11, the teachings of which are hereby incorporated by reference. The $TiO_2$ compounds may also be combined with polymers to form plastics products. Examples of polymers include polyethylene and polyvinyl chloride.

Alternatively, the resulting $TiO_2$ compounds may be further processed prior to using them as pigment products and incorporating them into plastics, paper and coating applications. For example, in order to improve the aesthetic qualities or other physical properties such as opacity whitening, the $TiO_2$ compounds may be further processed through a second series of treatments. These treatments include, but are not limited to leaching treatments (with reagents such as peracetic acid and the like) and calcining treatments with various chemical compounds such as calcium or zinc phosphate, which will also provide a whitening effect. The leaching and calcining treatments will produce "leached" and "calcined" products respectively. The treatments used in order to obtain the desired effects are known or easily determinable by persons skilled in the art. Thermal treatment steps may also be performed on the $TiO_2$ compounds in order to form particles of an appropriate size to facilitate the above-mentioned leaching or calcining steps. Each of these steps is well known or easily determinable to those skilled in the industry and may be performed alone, or in combination.

For example, a fraction of particles that have been processed according to the present invention and have a particle size distribution of from about 0.15 to about 0.40 microns may be chemically treated as described and/or calcined to improve the white color. Calcining may also be useful to adjust the anatase to rutile ratio of the naturally occurring material as desired. This intermediate pigment, which has been calcined, may then be treated chemically or surface treated to produce pigmentary products suitable for utilization in certain paper, plastic or coating applications.

c. Feedstock

Rather than using the $TiO_2$ compounds produced according to the present invention directly in industrial applications, the $TiO_2$ compounds can be blended with ore that is not suitable for the processes of the present invention. These blended ores may then be treated by either the sulfate or chloride processes. The use of such blended ores increases the efficiency of the sulfate and chloride processes. The resulting product of the sulfate and chloride processes is a $TiO_2$ pigment.

The typical operation of the "sulfate" process relies on the heat of reaction of sulfuric acid with iron in titania-containing ore to provide sufficient heat to form titanium sulfate. When used alone in the sulfate process, Tacna-type ore requires additional heat, and optionally higher reaction pressures to control and to initiate the reaction. However, a significant benefit of using Tacna-type concentrate as feedstocks in the sulfate process is that the amount of sulfuric acid required to manufacture each ton of $TiO_2$ is substantially reduced, thereby also reducing the volume of low value co-products, such as copperas or gypsum. Additionally, using this ore would substantially reduce wastes and effluent treatments, which would give rise to significant economic advantages in the production of sulfate-based titanium dioxide from prior art techniques.

Further, $TiO_2$ compounds obtained via the above-described steps, when blended with the "sulfate" or "chloride" processes, may improve the efficiency of the processes. Both of these processes are well known to persons skilled in the art. Blending of the $TiO_2$ compounds with titania for ore that is not Tacna-type ore for the chloride or sulfate processes may be accomplished by, for example, a conical blender.

Oversized or pigmentary fractions of $TiO_2$ compounds obtained from Tacna-type ore may also be prilled or agglomerated, as would be known to one of suitable skill in the art, to a size suitable for use as feedstock for the "chloride" process, where chlorine in a fluid bed reactor is reacted to produce titanium tetrachloride. The range of size of the titania ore useful in such applications is typically from about 50 to about 500 microns. Prilling and agglomerating may be used to make "prilled" and "agglomerated" products respectively.

d. Other Applications

The $TiO_2$ compounds may be used in many other different applications. For example, because the crystal structure of the titania in Tacna-type ore is often approximately 40% rutile and 60% anatase, and the iron content in the ore is roughly 500 PPM, certain catalyst applications, such as the so-called "$DeNO_x$" may be produced from the $TiO_2$ compounds with minimal processing of the subject ore. In this application, the natural iron content of the ore serves as redox centers. Further, the anatase to rutile ratio provides a near optimum ratio for photocatalytic activity. Additionally, the isolated titania would be useful as colored pigments, which may act as UV absorbers; typical applications are in the vinyl siding market. There, the iron content would serve as redox centers to increase durability without the need for multiple metal oxide surface treatments.

EXAMPLES

These following examples are set forth as preferred embodiments of the invention. These embodiments are merely illustrative and are not intended, and should not be construed, to limit the invention in any way.

Example 1

Obtaining $TiO_2$ Compounds Through the Combination of Polyethylene Glycol Extraction and Selective Flocculation Sixty grams of polyethylene glycol, PEG-2000 (Union Carbide) and 40 grams of sodium sulfate were added to a large glass beaker along with 300 grams of de-ionized water. Under moderate agitation, using a magnetic stirring apparatus, the chemicals were observed to separate into two immiscible liquid phases when agitation was ceased. To this liquid mixture, 10 grams of ground ore from Tacna, Peru was added to the beaker. The mixture was agitated moderately for about 30 minutes. After agitation, the ore in the mixture was observed to partition into the upper and lower liquid phases.

Using a separation funnel, the lower and upper phases were separated, filtered and washed with de-ionized water using 0.4 micron filter paper. Small amounts of the solids were subjected to EDAX analysis in order to determine the respective compositions. The titanium dioxide was found to be enriched in the lower, sodium sulfate—containing phase, while the silica was isolated in the upper phase, which contained the polyethylene glycol.

A second extraction experiment was performed on the solid material collected from the enriched $TiO_2$ phase from the first experiment. Subsequently, a third experiment was performed using the further $TiO_2$ enriched solid material collected from the second experiment.

The EDAX chemical analysis for each of the above 3-stage cascade extraction experiments are shown in Table 1.

TABLE 1

EDAX Chemical Analysis of the Tacna-type ore from Tacna, Peru and $TiO_2$ compounds

| Sample Description | $SiO_2$ (%) | $TiO_2$ (%) |
|---|---|---|
| Starting Ore | 89 | 10 |
| First Stage | 82 | 16 |
| Second Stage | 63 | 32 |
| Third Stage | 31 | 60 |

Depending on the concentration of the glycolic agent, and in principle, on its molecular weight and distribution, one of skill in the art would be able to provide a selective, enriching procedure for the titania values contained in the ore. Enhanced enrichments may yield as high a concentration as desired, depending on the amounts and ratios of the starting materials. Thus, the above process demonstrates that $TiO_2$ compounds suitable for commercial application can be obtained.

Example 2

Obtaining $TiO_2$ Compounds via Selective Flocculation

A quantity of Tacna-type ore from Tacna, Peru was mixed with sufficient water, sodium metasilicate and sodium polyacrylate to form a slurry. The Tacna-type ore contained approximately 7% $TiO_2$ by weight. The concentration of each reagent was about 0.25% weight percent based on the quantity of dry ore. The solids content of the slurry was about 60% and the pH was about 5.3.

The slurry was ground in a basket mill for about 10 minutes and subsequently treated with fatty acid and polyvalent salts. In this example, the fatty acid used was oleic acid and the polyvalent salt was $CaCl_2$. Other useful salts include, NaCl, $Na_2SO_4$, $Na_2CO_3$, KCl, $NaNO_3$, $NH_4Cl$. The oleic acid concentration was about 0.25 weight percent and $CaCl_2$ concentration was 0.2 weight percent based on the weight of dry ore. The slurry was aged for 20 minutes under moderate agitation. BETZ D1294™, a commercial flocculating agent produced by BetzDearborn, Trevose, Pa., was added so that the final solids content in the slurry was about 20 percent after addition of the polymer. The polymer addition was 0.02–0.03 weight percent based on the amount of dry ore. Gentle agitation was used to incorporate the polymer solution into the ore slurry wherein flocs were observed to rapidly settle out of the suspension on standing. The suspension was decanted to recover the titanium dioxide. See Table 2.

Example 3

Obtaining $TiO_2$ Compounds Using Commercial Sodium Polyacrylate

Commercial sodium polyacrylate was added to an aqueous slurry at a concentration of about 0.25 weight percent based on the powdered ore. The solids content of the slurry was approximately 40 percent with a pH of about 5.3.

The slurry was subsequently milled in a sandmill and treated with 0.25 weight percent oleic acid based on the weight of the dry ore. The slurry was aged for about 20 minutes under moderate agitation. The slurry was combined with sufficient water so that the final solids content of the slurry was 20% by weight. The silica flocculated and settled. The liquor containing the titanium dioxide was decanted. The starting ore was 11% $TiO_2$, and 89% $SiO_2$, the $TiO_2$ concentration in the product was 31% $TiO_2$, and 65% $SiO_2$.

Example 4

Obtaining $TiO_2$ Compounds Using AMP (2-amino-2-methyl-1-propanol)

Example 2 was repeated, except that AMP (2-amino-2-methyl-1-propanol) was used instead of sodium polyacrylate, and the Tacna-type ore contained approximately 22.68% $TiO_2$ by weight. Results are listed in Table 2 below.

Example 5

Obtaining $TiO_2$ Compounds Using Sodium Aluminate

Example 2 was repeated, except that sodium aluminate was used instead of sodium polyacrylate, and the Tacna-type ore contained approximately 22.68% $TiO_2$ by weight. Results are listed in Table 2 below.

Example 6

Obtaining $TiO_2$ Compounds Using Sodium Hexa Meta Phosphate (Calgon)

Example 2 was repeated, except that sodium hexa meta phosphate, Calgon, from Calgon Corporation, Pittsburgh, Pa., was used instead of sodium polyacrylate, and the Tacna-type ore contained approximately 7% $TiO_2$ by weight. Results are listed in Table 2 below.

Example 7

Obtaining $TiO_2$ Compounds Using BETZ POLYFLOC AE 1132™

Example 2 was repeated, except that BETZ POLYFLOC AE 1132™ was used instead of BETZ D 1294™, and the Tacna-type ore contained approximately 7% $TiO_2$ by weight. Results are listed in Table 2 below.

TABLE 2

Extraction of Titanium Dioxide from Tacna-type ore from Tacna, Peru

|  | $TiO_2$ % | $SiO_2$ % |
| --- | --- | --- |
| Series A |  |  |
| Starting Ore | 7 | 92 |
| Example 2 | 14 | 83 |
| Example 7 | 13 | 83 |
| Example 6 | 13 | 84 |
| Series B |  |  |
| Starting Ore | 15 | 82 |
| Example 4 | 27 | 67 |
| Example 5 | 24 | 70 |

The results for examples 2 and 4–7 are shown above in Table 2. They demonstrate that according to the present invention, one can increase the amount of titania relative to silica. Series A demonstrates an increase in the percentage of $TiO_2$ when the starting ore has a relatively low amount of $TiO_2$, and series B demonstrates an increase in the percentage of $TiO_2$ when the starting ore has a relatively high amount of $TiO_2$.

These examples illustrate that numerous flocculating agents will provide enrichment of Tacna-type ores. In order to increase further the percentage of $TiO_2$, one could repeat the steps described above or use them in combination with any other steps of the present invention. By repeating or combining these steps, one will be able to achieve titania levels above 50%.

Example 8

Obtaining $TiO_2$ Compounds Using Poly(acrylic Acid) Salt Dispersant in pH 5 Sodium Acetate/Acetic Acid Buffer Samples of Tacna-type ore from Tacna, Peru consisting of approximately 83.2% by weight silica and 14.9% by weight titania were subjected to a solids/liquid separation technique using a poly(acrylic) acid salt dispersant, a buffer system at pH 5, and a common mixing procedure.

A buffer solution of pH 5 was created with sodium acetate and acetic acid using the formulas outlined in *Lange's*

Handbook of Chemistry, 14th edition, pages 8.106 to 8.110. Two suspensions of approximately 90 ml were made with this buffer. The first contained 13.9% by weight of the sample ore in the buffer alone. The second contained 13.1% by weight of the sample of the ore in the buffer along with the poly(acrylic acid), sodium salt dispersant of $MW_n$ 2100 added in the amount of 4 milligram dispersant per gram of ore. Both suspensions were stirred using a Dispersmat® mixer, model AE3-M, with a 1" blade for 6 minutes at 4000 rpm in 250 ml HDPE beakers before being transferred into individual 100 ml mixing cylinders for a 24-hour settling period.

After 24 hours, the liquid phases of both cylinders were compared. The liquid phase of the ore/buffer suspension was almost completely clear since practically all of the material had settled to the bottom of the cylinder. However, the liquid phase of the ore/buffer/dispersant suspension was opaque and white with a suspended solid. X-ray analysis of this suspended material showed it to be 98.5% by weight silica with 0.5% by weight titania. This increase in the percentage of the silica in the suspended solid reflects a commensurate increase in the percentage of the titania in the settled material.

Example 9

Obtaining $TiO_2$ Compounds Using Tamol 1254™ Dispersant and Sodium Hydrogen Phosphate/Citric Acid Buffers A series of experiments as described in Example 8 were carried out using sodium hydrogen phosphate/citric acid buffers made at pH 5, 6 and 7. Approximately 90 ml of each buffer was mixed with 10 grams of Tacna-type ore from Tacna, Peru and 40 mg of Tamol 1254™, a commercial acrylic acid oligomer dispersant obtained from Rohm and Haas, Philadelphia, Pa. Each suspension was sonicated for 30 seconds in HDPE beakers using a ½" 400 Watt horn at 50% power. After approximately 15 minutes, the suspended and settled phases of each of the suspensions were collected for compositional analysis.

X-ray analysis of the suspended phase materials showed them to be 96.5% by weight silica/1.15% by weight titania in the pH 5 buffer, 90.4% by weight silica/2.33% titania in the pH 6 buffer, and 90.3% by weight silica/4.7% by weight titania in the pH 7 buffer. Likewise, X-ray analysis of the settled phase materials showed them to be 63.7% by weight silica/29.0% by weight titania in the pH 5 buffer, 67.5% by weight silica/24.1% titania in the pH 6 buffer, and 64.4% by weight silica/23.2% by weight titania in the pH 7 buffer. This enrichment with respect to the titania content in the settled material illustrates the effectiveness of this separation approach. It further demonstrates that the pH should be selected correctly and carefully in order to control the dispersant adsorption.

Having thus described and exemplified the invention with a certain degree of particularity, it should be appreciated that the following claims are not to be so limited but are to be afforded a scope commensurate with the wording of each element of the claim and equivalents thereof.

What is claimed is:

1. A process for obtaining $TiO_2$ compounds from an ore, said process comprising:

a. grinding an ore to form ground ore having particles of a size suitable to form an aqueous slurry, wherein said ore comprises at least 95% silica and titania, and either no iron or iron in an amount less than 0.5%;

b. combining the ground ore, water and a separating agent so as to form an aqueous slurry of constituents; and c. separating the constituents of the aqueous slurry to isolate the $TiO_2$ compounds, wherein during said process the titania is not subjected to a chemical conversion step and said $TiO_2$ compounds comprise at least 50% $TiO_2$.

2. A method of preparing feedstock for a $TiO_2$ pigment production process, the method comprising using $TiO_2$ compounds obtained from the process of claim 1.

3. The method of claim 2, wherein the $TiO_2$ compounds are blended with feedstock.

4. The method of claim 3, wherein the $TiO_2$ pigment production process is a chloride process.

5. The method of claim 3, wherein the $TiO_2$ pigment production process is a sulfate process.

6. In the process of producing $TiO_2$ pigment via a chloride process, the improvement comprising blending $TiO_2$ compounds obtained from the process of claim 1 into feedstock for the chloride process.

7. In the process of producing $TiO_2$ pigment via a sulfate process, the improvement comprising blending $TiO_2$ compounds obtained from the process of claim 1 into feedstock for the sulfate process.

8. The process of claim 1, wherein the grinding is accomplished by ball milling.

9. The process of claim 1, wherein the grinding is accomplished by media milling.

10. The process of claim 1, wherein the separating step comprises using a dispersant or surfactant.

11. The process of claim 1, wherein the separating step comprises using electrolytes.

12. The process of claim 1, wherein the separating step comprises using a polyglycolic compound.

13. The process of claim 12, wherein the polyglycolic compound is polyethylene glycol.

14. A process for obtaining leached $TiO_2$ compounds comprising obtaining $TiO_2$ compounds by the process of claim 1, and leaching the $TiO_2$ compounds to obtain leached $TiO_2$ compounds.

15. A process for obtaining calcined $TiO_2$ compounds comprising obtaining $TiO_2$ compounds by the process of claim 1, and calcining the $TiO_2$ compounds to obtain calcined $TiO_2$ compounds.

16. A process for obtaining agglomerated $TiO_2$ compounds comprising obtaining $TiO_2$ compounds by the process of claim 1, and agglomerating the $TiO_2$ compounds to obtain agglomerated $TiO_2$ compounds.

17. The process according to claim 1, wherein the ore comprises between about 4 weight percent and about 30 weight percent titania.

18. The process according to claim 17, wherein the titania comprises between about 15 weight percent and about 50 weight percent rutile crystals and between about 50 weight percent and about 85 weight percent anatase crystals.

* * * * *

UNITED STATES PATENT AND TRADEMARK OFFICE
CERTIFICATE OF CORRECTION

PATENT NO. : 6,713,038 B2  Page 1 of 1
DATED : March 30, 2004
INVENTOR(S) : Zhou, Lin et al.

It is certified that error appears in the above-identified patent and that said Letters Patent is hereby corrected as shown below:

<u>Title page,</u>
Item [73], Assignee, delete "Millenium Inorganic Chemicals, Inc." and insert
-- Millennium Inorganic Chemicals, Inc. --

Signed and Sealed this

Twenty-fifth Day of May, 2004

JON W. DUDAS
*Acting Director of the United States Patent and Trademark Office*